United States Patent [19]
Hemingway et al.

[11] Patent Number: 5,616,848
[45] Date of Patent: Apr. 1, 1997

[54] PLATE TESTING APPARATUS AND METHOD OF TESTING

[75] Inventors: Gregory Hemingway, Northville; James V. Legray, Sylvan Lake; John S. Hite, Sterling Heights, all of Mich.

[73] Assignee: Chrysler Corporation, Auburn Hills, Mich.

[21] Appl. No.: 407,540

[22] Filed: Mar. 20, 1995

[51] Int. Cl.⁶ .................................................. G01N 19/00
[52] U.S. Cl. ................................................ 73/838; 73/851
[58] Field of Search .......................... 73/826, 830, 838, 73/840, 849, 850, 851, 854, 860, 78, 81; 65/158

[56] References Cited

U.S. PATENT DOCUMENTS

| | | | |
|---|---|---|---|
| 1,180,506 | 4/1916 | Kirschbraun . | |
| 1,825,954 | 10/1931 | Hansard et al. . | |
| 2,645,937 | 7/1953 | Skalmusky et al. | 73/838 |
| 3,765,996 | 10/1973 | Munyon | 161/39 |
| 3,806,330 | 4/1974 | Martin | 65/158 |
| 3,927,558 | 12/1975 | Philippe et al. | 73/95 |
| 3,937,073 | 2/1976 | Steel | 73/101 |
| 4,347,735 | 9/1982 | Desai et al. | 73/849 |
| 4,393,700 | 7/1983 | Fabian | 73/150 |
| 4,393,717 | 7/1983 | Mason et al. | 73/821 |
| 4,589,288 | 5/1986 | Porter et al. | 73/849 |
| 4,625,563 | 12/1986 | Dawson et al. | 73/850 |
| 4,991,432 | 2/1991 | Houghton et al. | 73/852 |
| 5,507,189 | 4/1996 | Kim et al. | 73/838 |

*Primary Examiner*—Richard Chilcot
*Assistant Examiner*—Max H. Noori
*Attorney, Agent, or Firm*—Margaret A. Dobrowitsky

[57] ABSTRACT

An apparatus for evaluating the ultimate strength of a plate of material includes a fixture for holding the plate and a loading element for applying a load to the plate, The fixture has a support element for supporting the plate at first and second points on the plate. The loading element is capable of applying a load to the plate at a third point interior to the first and second points on the plate. Another embodiment is a method for evaluating the ultimate strength of a plate of material having a front side and a back side. The method includes supporting the plate at first and second points on the plate and gradually applying a load substantially perpendicular to the back side of the plate at a point on the plate interior to the first and second points. The load is applied to the plate until the plate breaks, and the amount of load at which the plate breaks is noted to evaluate the ultimate strength of the plate.

16 Claims, 3 Drawing Sheets

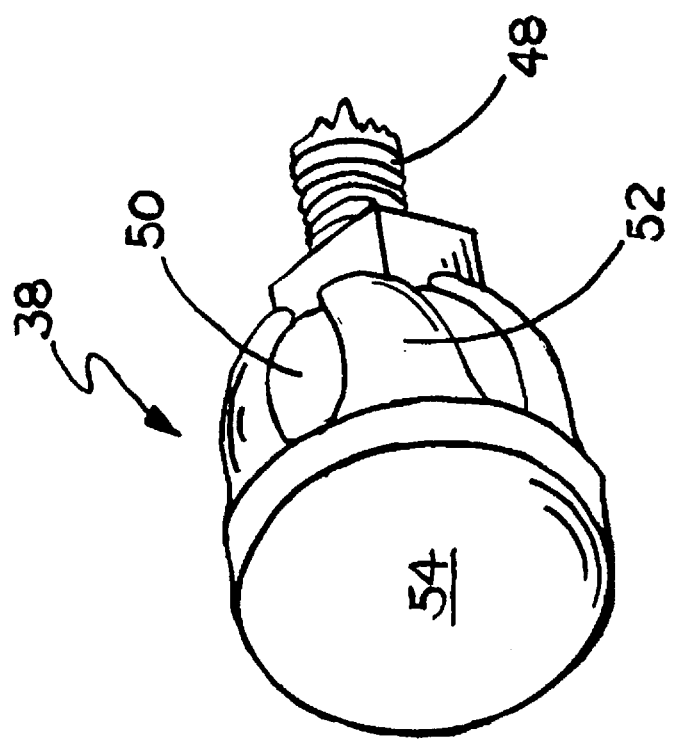

1

PLATE TESTING APPARATUS AND METHOD OF TESTING

BACKGROUND OF THE INVENTION

1. Field of the Invention

The present invention relates generally to a testing apparatus and a test method, and, more particularly, to a testing apparatus and test method for evaluating the ultimate strength of a plate of material.

2. Description of the Related Art

In various industries, it is desirable to be able to determine the quality of a part to be used in the final product as a way of evaluating different sources, different materials of construction, or different methods of manufacturing the part.

The part in consideration could be a plate of material, such as a plate of glass, to be used, e.g., as a windshield for an automobile. It would be useful to be capable of determining properties, such as the ultimate strength of a plate of material, so that a strong, high quality plate of material could be used in the product. It would also be useful to be capable of evaluating the ultimate strength variation of a series of plates to better meet today's demands of product quality control. An apparatus for determining such properties is advantageously quick and easy to use and provides reproducible results.

It is, therefore, one object of the present invention to provide a testing apparatus for evaluating the ultimate strength of a plate of material.

It is another object of the present invention to provide a testing apparatus for evaluating the ultimate strength of a plate of material, which apparatus is quick and easy to use and provides reproducible results.

It is yet another object of the present invention to provide a test method for evaluating the ultimate strength of a plate of material.

It is still another object of the present invention to provide a test method for evaluating the ultimate strength of a plate of material, which test method is quick and easy to do and provides reproducible results.

SUMMARY OF THE INVENTION

To achieve the foregoing objects, one embodiment of the present invention is a plate testing apparatus for evaluating the ultimate strength of a plate. The testing apparatus includes a fixture for holding the plate and a loading means for applying a load to the plate. The fixture has a support element for supporting the plate at first and second points on the plate. The loading means is capable of applying a load to the plate at a third point interior to the first and second points on the plate.

Typically, the plate has at least two opposite edges and the support element is capable of supporting the plate near the at least two opposite edges. The support element has a support surface, and, preferably, the support surface is adapted to allow the plate to slide on the support surface. It is also preferred that the support element is adapted to swivel to allow the plate to take on different conformities depending on the load applied. It is advantageous that the loading means has a plurality of rubber bumpers arranged linearly for contacting the plate, and that the bumpers are individually position-adjustable in the direction of the load so that the bumpers may be arranged to contact the plate when desired even when the plate is curved.

Another embodiment of the present invention is a method for evaluating the ultimate strength of a plate. The method includes supporting the plate at first and second points on the plate and gradually applying a load substantially perpendicular to the plate at a point on the plate interior to the first and second points. The load is applied to the plate until the plate breaks, and the amount of load at which the plate breaks is noted to evaluate the ultimate strength of the plate.

Other objects, features, and advantages of the present invention will be readily appreciated as the same becomes better understood after reading the subsequent description taken in conjunction with the appendant drawings.

BRIEF DESCRIPTION OF THE DRAWINGS

FIG. 3 is a perspective view of a support element used in the plate testing apparatus of FIG. 1.

DESCRIPTION OF THE PREFERRED EMBODIMENT(S)

Figure 1:
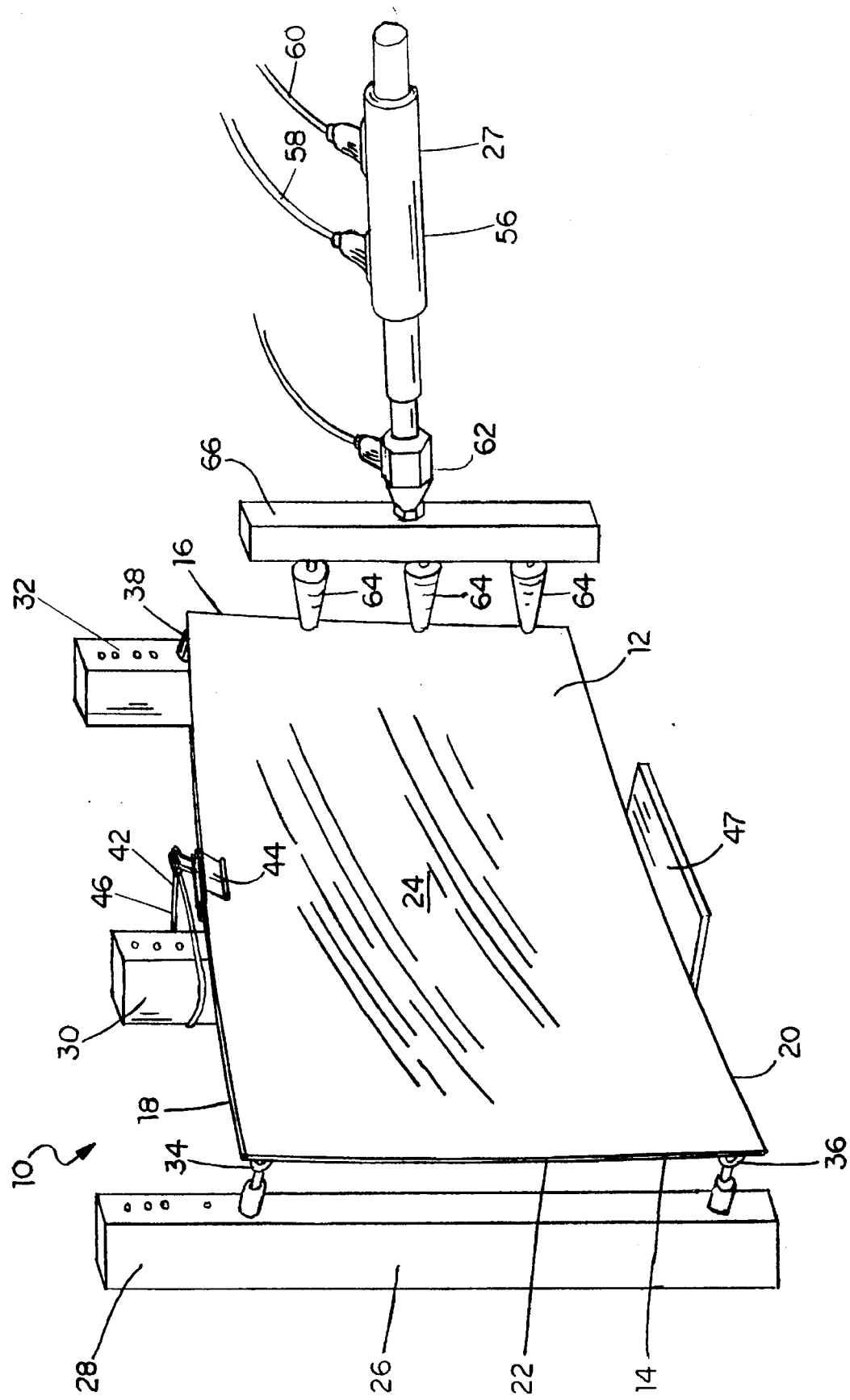
FIG. 1 is a perspective view of a plate testing apparatus according to the present invention shown with a plate fixed thereto for testing.
Figure 2:
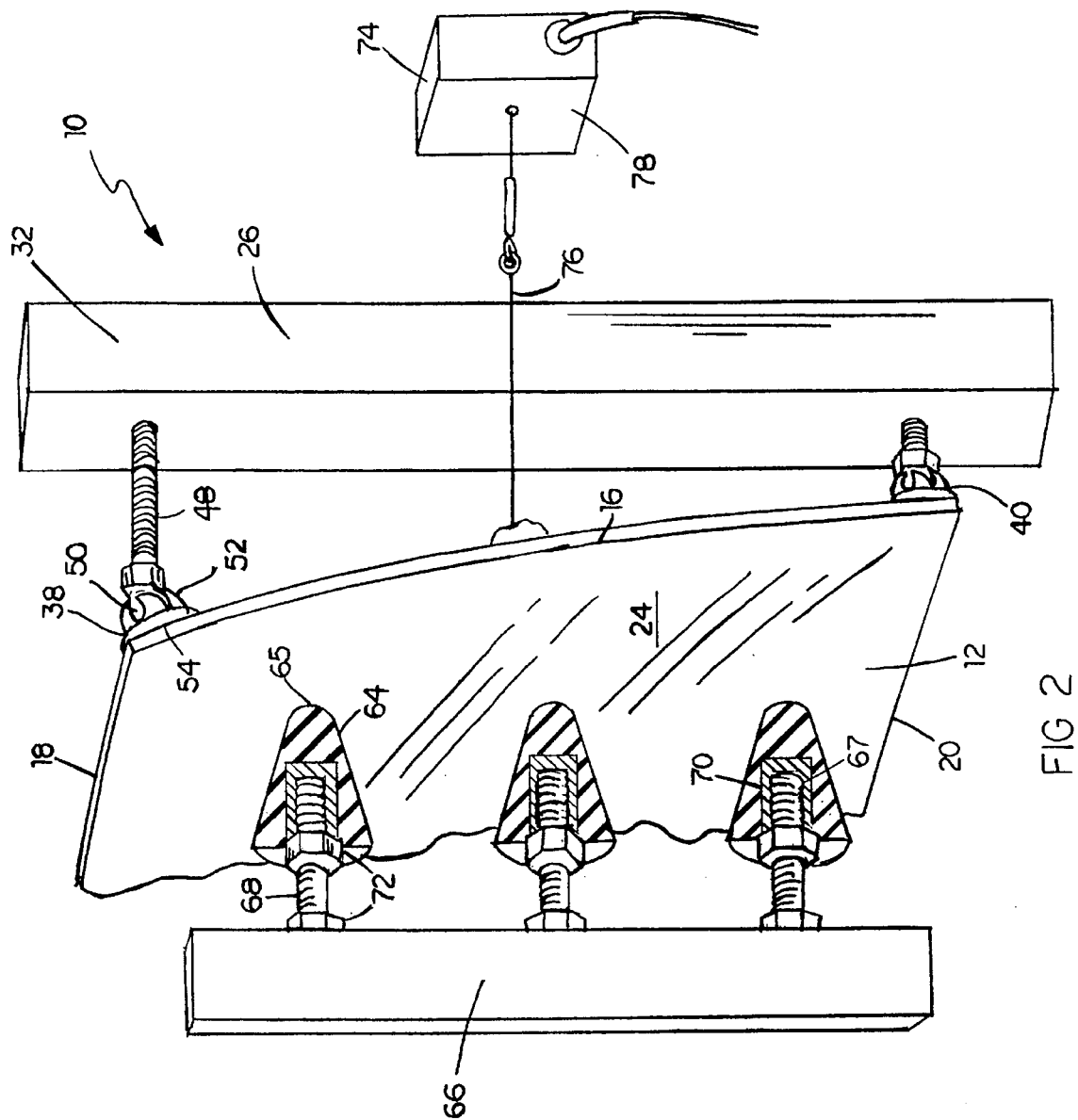
FIG. 2 is a perspective view of a portion of the plate testing apparatus of FIG. 1 showing a displacement measuring device attached to the plate.

Referring to FIGS. 1 and 2, a plate testing apparatus is generally indicated by reference numeral 10. Plate testing apparatus 10 evaluates the ultimate or tensile strength of a plate of material by applying a continuously-increasing load to the plate of material until the plate breaks and noting the amount of load applied when the plate breaks. The test performed using testing apparatus 10 is considered a destructive test since the plate of material is destroyed by breaking the plate during the test.

FIG. 1 also shows plate 12 attached to plate testing apparatus 10. Plate 12 has vertical opposite edges 14 and 16, horizontal top edge 18, horizontal bottom edge 20, front side 22, and back side 24. Plate 12 is rectangular and flat but may be non-rectangular and contoured, such as those used as windshields for automobiles.

Plate 12 may be formed of essentially any material. The testing apparatus is especially useful for testing plates formed of a brittle material, such as glass and/or plastic. A plate of material is considered to be a piece of material in which the thickness is not more than one-fourth of the least transverse dimension. In other words, the thickness of a plate of material is not more than one-fourth the width or the length of the plate. This definition is a standard definition of "plate" and may be found on page 324 of *Formulas for Stress and Strain, 5th Edition*, by Raymond Roark, et al., published by McGraw-Hill Book Co., New York, N.Y. 1975.

Plate testing apparatus 10 includes fixture 26 for holding plate 12 and loading means 27 for applying a load to the plate. Fixture 26 includes three stanchions 28, 30, and 32. Stanchions 28 and 32 are present to provide support to front side 22 of plate 12. Stanchion 28 has support elements 34 and 36 thereon, and stanchion 32 has support elements 38 and 40 thereon. Support element 34 supports plate 12 near top edge 18 and vertical edge 14, support element 36 supports plate 12 near bottom edge 20 and vertical edge 14, support element 38 supports plate 12 near top edge 18 and vertical edge 16, and support element 40 supports plate 12 near bottom edge 20 and vertical edge 16. That is, support elements 34, 36, 38, and 40 support plate 12 near the plate's four corners. Support elements 34, 36, 38, and 40 are present to keep plate 12 from displacing forward or in the direction of front side 22.

Stanchions 28, 30, and 32 are merely one form of a structure for supporting plate 12. The stanchions could be replaced by another structure, e.g., a rigid framework, which supplies a rigid member for attachment of the support elements. In addition, other arrangements of the support elements are possible to use in the present invention. For example, three support elements may be used, such as, two near edge 14 and one near edge 16. Alternatively, a single support element which follows the entire periphery of the plate may be used.

For discussion purposes, a legend is included in FIG. 1 referencing dimensions x, y, and z. Dimension x is perpendicular to side 24 of supported plate 12 and dimensions y and z are parallel with side 24 of supported plate 12. If supported plate 12 moves horizontally and parallel to side 24, the movement is considered to be in the y dimension. If supported plate 12 moves vertically and parallel to side 24, the movement is considered to be in the z dimension.

Fixture 26 also includes holding means 42 for holding plate 12 so that it does not fall backward or in the direction of back side 24. Holding means 42 includes clip 44 and flexible band 46. Clip 44 is attached to top edge 18 of plate 12, and flexible band 46 is attached to clip 44 and stanchion 30. Support elements 34, 36, 38, and 40 together with holding means 42 are present to constrain plate 12 one degree of freedom, i.e., to keep plate 12 from moving in the x dimension. Holding means 42 employs a movable element like flexible band 46 to allow plate 12 to move in the y and z direction if necessary as a load is applied to the plate. Other holding means will be apparent.

During testing, plate 12 rests on the horizontal surface upon which testing apparatus 10 is assembled. Wooden block 47 is placed beneath plate 12 to provide a non-scratching surface on which the plate rests.

Support element 38 will now be described in detail and is representative of support elements 34, 36, and 40. As is best seen in FIGS. 2 and 3, support element 38 includes means 48 for attaching support element 38 to stanchion 32 which may be any suitable known means, such as a threaded bolt. Means such as a threaded bolt allows the support element to be adjusted in or out from its respective stanchion so there is some adjustability allowed. Support element 38 also includes spherical element 50, socket element 52, and support surface 54.

Spherical and socket elements 50 and 52 constitute a spherical joint and flat pad which allows support surface 54 to swivel so that plate 12 can bend as needed from an applied load with minimal unwanted stresses to the plate. Other designs for the support elements, such as reversing the position of the spherical element and the socket element, would also allow the support elements to swivel and would be suitable for use in the present invention.

Support surface 54 is adapted to allow plate 12 to slide on the support surface so that when a load is applied to plate 12, plate 12 can move and bend as needed with minimal friction as friction would cause unwanted stresses to the plate. To possess such a quality, support surface 54 is preferably formed of a material such that the static coefficient of friction between support surface 54 and plate 12 is less than about 0.8. For example, the static coefficient of friction between glass and metal is typically from about 0.5 to about 0.7. Therefore, it would be suitable to have support surface 54 formed of metal if plate 12 is formed of glass. An exemplary suitable metal is cast iron which has been ground smooth on the support surface. In addition, support surface 54 is circular having no sharp edges which could inadvertently scratch plate 12. Other ways of achieving the desirable coefficient of friction between plate 12 and support surface 54 is through the use of lubricants or other low-friction coatings on the support surface.

Loading means 27 is present to apply a load substantially perpendicularly to back side 24 of plate 12 at a point interior on plate 12 to at least two points where plate 12 is supported. For plate 12, loading means 27 may apply a load anywhere between the points on plate 12 which are supported by support elements 34, 36, 38, and 40.

Loading means 27 includes loading ram 56 which has fluid lines 58 and 60, load cell 62, and three bumpers 64, a top bumper, a middle bumper, and a bottom bumper. Bumpers 64 are arranged linearly and vertically and mounted on bar 66. Any means for supporting loading ram 56 may be used in the present invention (supporting means is not shown in the figures). It is desirable that the supporting means for loading ram 56 be height-adjustable so that the load may be directed to the desired location on plate 12. Loading ram 56 is shown as a hydraulically-driven ram. Fluid lines 58 and 60 supply incompressible fluid to loading ram 56 to control the linear position of bar 66, that is, its position toward or away from plate 12. Alternative to using hydraulics, the loading ram could be, e.g., air-driven, electrically-driven, or manually-driven.

Load cell 62 detects the amount of load being applied to plate 12 and is preferably electrically-connected to a recording device (not shown) for recording the load versus time on any suitable media, e.g., an x-y plot, a peak hold digital display meter, or an analog tape.

Bumpers 64 are preferably formed of rubber, e.g., urethane rubber, so that they conform to plate 12 and do not scratch the plate on contact. Bumpers 64 have tips 65 which are designed to contact plate 12. Bumpers 64 are arranged linearly to provide a relatively uniform linear stress distribution on plate 12. Each bumper 64 is individually position-adjustable in the direction of the load so that the bumpers may be adjusted to contact plate 12 at the desired time even when plate 12 is contoured. For example, when plate 12 is curved so that back side 24 is curved inward toward front side 22, it is desirable to adjust the middle bumper 64 to extend beyond the other two bumpers in the direction of plate 12. The position-adjustability also allows for more variation in the testing procedure.

Bumpers 64 are made position-adjustable by providing each bumper 64 with a threaded bore 67 and mounting bumpers 64 on threaded bolts 68 which extend from bar 66. In FIG. 2, bumpers 64 are shown in cross section to show that threaded bores 67 are provided by threaded metal inserts 70 inserted in bumpers 64 for easier and longer-lasting use on the threaded bolts. To secure bumpers 64 in position on bolts 68, two nuts 72 are provided for each bumper 64. One nut is tightened against bumper 64 and the other is tightened against bar 66.

As shown in FIG. 2, plate testing apparatus 10 includes displacement measuring device 74 which is present to measure movements in plate 12 during testing. During testing, plate 12 may deflect by bending due to the applied load. Once a large enough load is applied to cause plate 12 to break, a larger change in movement results. Displacement measuring device 74 may be made to detect all movements of plate 12, and the largest movement detected would normally correspond to the point of breakage.

Displacement measuring device 74 is shown as being a string potentiometer. String 76 is attached to plate 12 at edge 16 by any suitable means, e.g., with glue, as shown. String 76 leads to box 78 which contains a cell for measuring displacement. The string potentiometer is electrically-connected to a recording device (not shown) in which displacement versus time may be recorded. Alternative to using a string potentiometer, a spring-loaded device may be used in the present invention. It is useful to combine the recordings of displacement and load so that the load at breakage is more easily determined since normally it is the load at which time a large displacement discontinuity is recorded.

The plate testing device is shown and described so that the plate is held vertically for testing. Alternatively, the plate testing device could be made so that the plate rests horizontally on at least one support element. In this fashion, elements such as clip 44 and flexible band 46 would not be needed as gravity would keep the plate from moving upwards.

The following is a description of a method of using plate testing apparatus 10 for evaluating the ultimate strength of plate 12 in which plate 12 is a windshield in which the windshield is a curved plate of glass. First, the middle bumper 64 is removed from bar 66. Then, top and bottom bumpers 64 are adjusted, using a level, until their tips 65 are in a vertical plane. Next, plate 12 is installed vertically in fixture 26 so that bottom edge 20 rests on a horizontal surface and plate 12 is supported by support elements 34, 36, 38, and 40 and held in place by flexible band 46, and the curve of plate 12 is such that back side 24 is curved inwardly while front side 22 bulges outwardly.

The height of loading ram 56 is then adjusted so that bumpers 64 will contact plate 12 at the desired points. Typically, it is desirable to test plate 12 at each of the vertical edges 14 and 16. For this testing, bumpers 64 typically contact plate 12 near edge 14 or 16 between support elements 34, 36, 38, and 40 and middle bumper 64 contacts the middle of plate 12. Preferably, the top and bottom bumpers 64 should contact plate 12 at the inside edge of the windshield frit which is typically approximately 0.125 inches inboard of the edge of plate 12. For purposes of discussion, the test method will be described in which edge 14 will be tested first.

Loading ram 56 is then extended until one of either the top or bottom bumpers 64 touches plate 12. Upper and lower support elements 34 and 36 are then adjusted until top and bottom bumpers 64 touch plate 12 simultaneously. Then loading ram 56 is retracted and the middle bumper 64 is reinstalled. Middle bumper 64 is adjusted so it will contact the plate 0.03 inches before the top and bottom bumpers 64 contact the plate.

Typically, a load is then applied to plate 12 at a maximum rate of 5 pounds per second until the plate breaks, at which point the load is noted. If the test is being used as a screening test in which the test is to determine if a plate can withstand a certain load without breaking, then the load may be applied at a faster rate. However, during such a screening test, the maximum load should be held for at least 3 seconds to allow for any friction to be overcome and for the full stress to be reached.

The above-described procedure is then repeated by testing edge 16.

The load at breakage correlates to the ultimate strength of the plate. To evaluate a series of plates for their variation in ultimate strength, one may merely compare the loads at breakage. However, if one wants to use the apparatus or test method of the present invention to determine the true ultimate strength of a plate, a load vs. stress curve may be generated for a particular apparatus and test method by calibrating the apparatus and test method by, e.g., strain gaging or finite element analysis. It is recommended that several tests be conducted on a series of plates that are under study so that a mean ultimate strength and standard deviation may be obtained.

Accordingly, the plate testing apparatus and method of the present invention are useful for evaluating the ultimate strength of a plate of material which apparatus is quick and easy to use and which method is quick and easy to do and both provide reproducible results.

The present invention has been described in an illustrative manner. It is to be understood that the terminology which has been used is intended to be in the nature of words of description rather than of limitation. Many modifications and variations of the present invention are possible in light of the above teachings. Therefore, within the scope of the appended claims, the present invention may be practiced otherwise than as specifically described.

What is claimed is:

1. A plate testing apparatus for evaluating the ultimate strength of a plate of material by causing movement and breakage of the plate of material, the apparatus comprising:

a fixture for holding the plate, the fixture having a support element for supporting the plate at first and second points on the plate, the support element being adapted to swivel to allow the plate to bend from an applied load and having a support surface which is adapted to allow the plate to slide on the support surface; and loading means for applying a load to the plate at a third point interior to the first and second points on the plate.

2. A method for evaluating the ultimate strength of a plate of material, the plate having a front side and a back side, the method comprising:

supporting the plate at first and second points on the plate;

adjusting a loading means having a top bumper, a middle bumper, and a bottom bumper, the top, middle, and bottom bumper being arranged linearly, the adjusting being conducted so that the middle bumper is closer to the plate than are the top and bottom bumpers;

gradually applying a load substantially perpendicular to the back side of the plate with the bumpers which are positioned at points on the plate interior to the first and second points, the load being applied to the plate until the plate breaks; and noting the amount of load at which the plate breaks to evaluate the ultimate strength of the plate.

3. The apparatus of claim 1, wherein the support element includes a spherical joint and flat pad to allow the support element to swivel.

4. The apparatus of claim 1, further comprising a displacement measuring device for measuring the movement of the plate while testing the ultimate strength of the plate.

5. The apparatus of claim 1, wherein the plate has at least two opposite edges and the support element is capable of supporting the plate on the at least two opposite edges.

6. A plate testing apparatus for evaluating the ultimate strength of a plate of material by causing movement and breakage of the plate of material, the plate having at least two opposite edges, the apparatus comprising:

a fixture for holding the plate, the fixture having a support element for contacting the plate at first and second points, the support element being capable of supporting the plate on the at least two opposite edges of the plate, the support element having a support surface, the support surface being adapted to allow the plate to slide on the support surface, the support element being adapted to swivel to allow the plate to take on different conformations depending on the load applied, and loading means capable of applying a load to the plate at any point interior to the first and second points on the plate, the loading means having a plurality of bumpers arranged linearly for contacting the plate, the bumpers being individually position-adjustable in the direction of the load.

7. The apparatus of claim 1, wherein the support surface is formed of a material such that the static coefficient of friction between the support surface and the plate is less than about 0.8.

8. The apparatus of claim 1, wherein the support surface is formed of metal.

9. The apparatus of claim 1, wherein the loading means has a plurality of bumpers arranged linearly for contacting the plate.

10. The apparatus of claim 9, wherein the bumpers are formed of rubber.

11. The apparatus of claim 9, wherein the bumpers are individually position-adjustable in the direction of the load.

12. The apparatus of claim 6, wherein the bumpers are formed of rubber.

13. The apparatus of claim 6, wherein the support element includes a spherical joint and flat pad to allow the support element to swivel.

14. The apparatus of claim 6, further comprising a displacement measuring device for measuring the movement of the plate while testing the ultimate strength of the plate.

15. The apparatus of claim 6, wherein the support surface is formed of a material such that the static coefficient of friction between the support surface and the plate is less than about 0.8.

16. The apparatus of claim 6, wherein the support surface is formed of metal.

* * * * *